United States Patent
LaMuraglia

(10) Patent No.: US 6,520,981 B1
(45) Date of Patent: Feb. 18, 2003

(54) SIGNIFICANCE OF DOSIMETRY IN PHOTODYNAMIC THERAPY OF INJURED ARTERIES

(75) Inventor: Glenn Michael LaMuraglia, Winchester, MA (US)

(73) Assignee: The General Hospital Corporation, Boston, MA (US)

(*) Notice: Subject to any disclaimer, the term of this patent is extended or adjusted under 35 U.S.C. 154(b) by 115 days.

(21) Appl. No.: 09/678,174

(22) Filed: Oct. 2, 2000

Related U.S. Application Data

(60) Provisional application No. 60/157,325, filed on Oct. 1, 1999, and provisional application No. 60/157,409, filed on Oct. 1, 1999.

(51) Int. Cl.$^7$ .............................................. A61B 9/01
(52) U.S. Cl. ........................... 607/89; 607/92; 606/15; 606/7; 606/3; 604/20
(58) Field of Search ........................ 607/89, 88, 92, 607/94; 606/15, 194, 28, 7, 14, 3, 16; 604/913, 20

(56) References Cited

U.S. PATENT DOCUMENTS

| | | | | |
|---|---|---|---|---|
| 5,019,075 A | * | 5/1991 | Spears et al. | 606/7 |
| 5,053,033 A | * | 10/1991 | Clarke | 606/3 |
| 5,354,324 A | * | 10/1994 | Gregory | 607/92 |
| 5,417,653 A | * | 5/1995 | Sahota et al. | 604/20 |
| 5,632,767 A | * | 5/1997 | Sinofsky | 607/89 |
| 5,776,174 A | * | 7/1998 | Van Tassel | 607/89 |
| 5,876,426 A | * | 3/1999 | Kume et al. | 607/88 |
| 6,107,466 A | | 8/2000 | Hasan et al. | 530/351 |

FOREIGN PATENT DOCUMENTS

| | | | | |
|---|---|---|---|---|
| WO | WO 01/35996 A2 | 5/2001 | .......... | A61K/41/00 |
| WO | WO 01/35997 A2 | 5/2001 | .......... | A61K/41/00 |

OTHER PUBLICATIONS

Adili et al. "Local delivery of photosensitizing drugs in arteries: A novel approach to photodynamic therapy for the prevention of intimal hyperplasia" *SPIE* 2395: 402–408 (1995).

Coats et al. "Tin ethyl etipurpurin significantly inhibits vascular smooth muscle cell proliferation in vivo", *Biochem. Cell Biol.* 74: 325–331 (1996).

Heckenkamp et al. "Local photodynamic action of methylene blue favorably modulates the postinterventional vascular wound healing response" *Journal of Vascular Surgery* 31 (61): 1168–1177 (2000).

Hsiang et al. "Dosage and timing of Photofrin to photodynamic therapy of intimal hyperplasia" *Cardiovascular Surgery* 3 (5): 489–494 (1995).

Lambert et al. "Local drug delivery catheters: functional comparison of porous and microporous designs" *Coronary Artery Disease* 4 (5): 469–475 (1993).

Orth et al. "Methylene blue mediated photodynamic therapy in experimental colorectal tumors in mice" *Journal of Photochemistry and Photobiology B: Biology* 57: 186–192 (2000).

Vincent et al. "Effects of Benzoporphyrin Derivative Monoacid on Balloon Injured Arteries in a Swine Model of Restenosis" *SPIE* 2671: 72–77 (1996).

(List continued on next page.)

Primary Examiner—Teresa Walberg
Assistant Examiner—Fadi H. Dahbour
(74) Attorney, Agent, or Firm—Nutter McClennen & Fish, LLP

(57) ABSTRACT

Photodynamic therapy (PDT), the light activation of methylene blue or benzoporphyrin derivatives to produce free-radicals, was shown in vivo to inhibit intimal hyperplasia (IH) and restenosis. The present invention provides an effective clinical approach for PDT treatment which modulates the vascular intervention injury healing response.

15 Claims, 6 Drawing Sheets

OTHER PUBLICATIONS

Adili, F., et al., "Photodynamic Therapy with Local Photosensitizer Delivery Inhibits Experimental Intimal Hyperplasia," *Lasers in Surg. Med.*, vol. 23, 23; 263–273 (1998).

Adili, F., et al., "Significance of Dosimetry in Photodynamic Therapy of Injured Arteries: Classification of Biological Responses," *Photochem. Photobio.*, vol. 70, No. 4; 663–668 (1999).

Bryant, S.R., et al., "Vascular Remodeling in Response to Altered Blood Flow is Mediated by Fibroblast Growth Factor–2," *Cir. Res.*, vol. 84; 323–328 (1999).

Camenzkind, E., et al., "Use of Locally Delivered Conventional Drug Therapies," *Semin. Interv. Cardiol.*, vol. 1:67–76 (1996).

Clowes, A.W., "Pathologic Intimal Hyperplasia as a Response to Vascular Injury and Reconstruction," *Vascular Surgery*, vol. 1; 285–295 (1995).

Coleman, M.D., et al., "Drug–Induced Methaemoglobinaemia," *Pharmacoepidemiology*, vol. 14, No. 6; 394–405 (Jun. 1996).

Davies, M.G., et al., "Pathobiology of Intimal Hyperplasia," *British. J. of Surg.*, vol. 81; 1254–1269 (1994).

DeYoung, M.B., "Gene Therapy for Restenosis. Are We Ready?," *Circ. Res.*, vol. 82; 306–313 (1998).

Dubbleman, T., et al., "Photodynamic Therapy: Membrane and Enzyme Photobiology," *Photodynamic Therapy. Basic Principles and Clinical Applications*, 37–46 (1992).

Eton, D., et al., "Photodynamic Therapy," *Arch Surg.*, vol. 130; 1098–1103 (1995).

Evanko, S.P., et al., "Formationof Hyaluronan–and Versican–Rich Pericellular Matrix is Required for Proliferation and Migration of Vascular Smooth Muscle Cells," *Aterioscler. Thromb. Vasc. Biol.*, vol. 19; 1004–1013 (1999).

Evanko, S.P., et al., "Proteoglycan Distribution in Lesions of Atherosclerosis Depends on Lesion Severity, Structural Characteristics, and the Proximity of Platelet–Derived Growth Factor and Transforming Growth Factor–$\beta$," *Amer. J. Path.*, vol. 152, No. 2; 533–546 (Feb. 1998).

Fisher, A., et al., "Clinical and Preclinical Photodynamic Therapy," *Lasers Surg. Med.*, vol. 17; 2–31 (1995).

Forrester, J., et al., "A Paradigm for Restenosis Based on Cell Biology: Clues for the Development of New Preventive Therapies," *JACC*, vol. 17, No. 3; 758–769 (Mar. 1, 1991).

Geary, R.L., et al., "Wound Healing: A Paradigm for Lumen Narrowing After Arterial Reconstruction," *J. Vasc. Surg.*, vol. 27, No. 1; 96–108 (Jan. 1998).

Gonschior, P., et al., "Local Photodynamic Therapy Reduces Tissue Hyperplasia in an Experimental Restenosis Model," *Photochem. Photobio.*, vol. 64, No. 5; 758–763 (1996).

Grant, W.E., et al., "The Effect of Photodynamic Therapy on the Mechanical Integrity of Normal Rabbit Carotid Arteries," *Laryngoscope*, vol. 105; 867–871 (Aug. 1995).

Grant, W.E., et al., "Photodynamic Therapy of Normal Rat Arteries After Photosensitisation Using Disulphonated Aluminum Phthalocyanine and 5–Aminolaevulinic Acids," *Br. J. Cancer.*, vol. 70; 72–78 (1994).

Grinnell, F., "Fibroblast, Myofibroblasts, and Wound Contraction," *J. Cell Bio.*, vol. 124; No. 4; 401–404 (Feb. 1994).

Henderson, B.W., et al., "How Does Photodynamic Therapy Work?," *Photochem. Photobio.*, vol. 55, No. 1; 145–157 (1992).

Henderson, D.J. et al., "Versican Expression in Associated with Chamber Specification, Septation, and Valvulogenesis in the Developing Mouse Heart," *Circ. Res.*, vol. 83; 523–532 (1998).

Hilf, R., "Cellular Targets of Photodynamic Therapy as a Guide to Mechanisms," *Photodynamic Therapy. Basic Principles and Clinical Applications*, 47–54 (1992).

Hsiang, Y.N., et al., "Photodynamic Therapy for Atherosclerotic Stenoses in Yucatan Miniswine," *JCC*, vol. 37, No. 2; 148–152 (Apr. 1994).

Hsiang, Y.N., et al., "Preventing Intimal Hyperplasia with Photodynamic Therapy Using an Intravascular Probe," *Ann. Vasc. Surg.*, vol. 9, No. 1; 80–86 (1995).

Hsiang, Y.N., et al., "Preventing Restenosis in Atherosclerotic Miniswine with Photodynamic Therapy," *SPIE*, vol. 2395; 384–389 (1995).

Huehns, T.Y., et al., "Adventia as a Target for Intravascular Local Drug Delivery," *Heart*, vol. 75; 537–538 (1996).

Ito, K., et al., "Multiple Forms of Mouse PG–M, a Large Chondroitin Sulfate Proteoglycan Generated by Alternative Splicing," *J. Bio. Chem.*, vol. 270, No. 2; 958–965 (1995).

Jenkins, MP., et al., "Intra–Arterial Photodynamic Therapy Using 5–ALA in a Swine Model," *Eur. J. Vas. Endovasc. Sur.*, vol. 16; 284–291 (1998).

Kagan, S.A., et al., "Mediators of Restenosis," *Surg. Clinics of N. Amer.*, vol. 78, No. 3; 481–501 (Jun. 1998).

Kishimoto, J., et al., "Cellular Localization of Putative Odorant Receptor mRNAs in Olfactory and Chemosensory Neurons: a Non–Radioactive In Situ Hybridization Study," *Mol. Brain Res.*, vol. 33–39 (1994).

Kypreos, K.E., "Basic Fibroblast Growth Factor–Induced Decrease in Type I Collagen Gene Transcription is Mediated by B–Myb[1]," *Cell Growth & Differentiation*, vol. 9; 723–730 (Sep. 1998).

Lambert, C.R., et al., "Microporous Infusion Catheter," *Semin. Intervent. Cardiol.*, vol. 1:30–31 (1996).

LaMuraglia, G.M., et al., "Photodynamic Therapy Inactivates Extracellular Matrix–Basic Fibroblast Growth Factor: Insights to its Effect on the Vascular Wall," *J. Vasc. Surg.*, vol. 26, No. 2; 294–301 (Aug. 1997).

LaMuraglia, G.M., et al., "Photodynamic Therapy Inhibition of Experimental Intimal Hyperplasia: Acute and Chronic Effects," *J. Vas. Surg.*, vol. 19, No. 2; 321–331 (Feb. 1994).

LaMuraglia, G.M., et al., "Chloroaluminum Sulfonated Phthalocyanine Partitioning in Normal and Intimal Hyperplastic Artery in the Rat," *Am. J. Pathol.*, vol. 142, No. 6; 1898–1905 (Jun. 1993).

Larsson, L.I., et al., "Optimization of Non–Radioactive In Situ Hybridization: Image Analysis of Varying Pretreatment, Hybridization and Probe Labeling Conditions," *Histochem.*, vol. 93; 347–354 (1990).

Laurent, G.J., "Dynamic State of Collagen: Pathways on Collagen Degradation In Vivo and Their Possible Role in Regulation of Collagen Mass," *Amer. J. Physio.*, vol. 252; C1–C9 (1987).

Li, S.W., et al., "The Complete cDNA Coding Sequence for the Mouse Pro $\alpha$1(1) Chain of Type I Procollagen," *Matrix Bio.*, vol. 14; 593–595 (1994).

Matsuura, R. et al., "Deposition of PG–M/Veriscan is a Major Cause of Human Coronary Restenosis After Percutaneous Transluminal Coronary Angioplasty," *J. Path.*, vol. 180; 311–316 (1996).

Meyer, B.J., et al., "Local Delivery of r–Hirudin by a Double–Balloon Perfusion Catheter Prevents Mural Thrombosis and Minimizes Platelet Deposition After Angiolasty," *Circulation*, vol. 90, No. 5; 2474–2480 (Nov. 1994).

Morales, T.G., et al., "Methylene Blue Staining for Intestinal Metaplasia of the Gastric Cardia with Follow–up for Dysplasia," *Gastrointest. Endosc.*, vol. 48, No. 1; 26–31 (1998).

Nyamekye, I., et al., "Inhibition of Intimal Hyperplasia in Balloon Injured Arteries with Adjunctive Phthalocyanine Sensitised Photodynamic Therapy," *Eur. J. Vasc. Endovasc. Surg.*, vol. 11; 19–28 (1996).

Nyamekye, I., et al., "Photodynamic Therapy of Normal and Balloon–Injured Rat Carotid Arteries Using 5–Amino–Levulinic Acid" *Circulation*, vol. 91, No. 2; 417–425 (Jan. 15, 1995).

Ortu, P., et al., "Photodynamic Therapy of Arteries. A Novel Approach for Treatment of Experimental Intimal Hyperplasia," *Circulation*, vol. 85, No. 3; 1189–1196 (Mar. 1992).

Pass, H.I., "Photodynamic Therapy in Oncology: Mechanisms and Clinical Use," *J. Natl. Cancer Inst.*, vol. 85, No. 6, 443–456 (Mar. 17, 1993).

Reidy, M., et al., "Factors Controlling the Development of Arterial Lesions After Injury," *Circulation*, vol. 86, No. 6; Supplement III: III–43—III–46 (Dec. 1992).

Rockson, R.G., "Photoangioplasty of Human Atherosclerosis Using Antrin Photosensitizer," [Abstract] *Photochem. Photobio.*, vol. 67:79S (1998).

Rogers, C., et al., "Balloon–Artery Interactions During Stent Placement. A Finite Element Analysis Approach to Pressure, Compliance, and Stent Design as Contributors to Vascular Injury," *Circ. Res.*, vol. 84; 378–383 (1999).

Ruck, A., et al., "Nonlinear Dynamics of Intracellular Methylene Blue During Light Activation of Cell Cultures," *Photochem. Photobiol.*, vol. 66, No. 6:837–841 (1997).

Schmidt–Erfurth, U., et al., "In Vivo Uptake of Liposomal Benzpporphin Derivative and Photothrombosis in Experimental Corneal Neovascularization," *Lasers Surg. Med.*, vol. 17; 178–188 (1995).

Schonherr, E., et al., "Effects of Platelet–derived Growth Factor and Transforming Growth Factor–$\beta1$ on the Synthesis of a Large Versican–like Chondroitin Sulfate Proteoglycan by Arterial Smooth Muscle Cells," *J. Bio. Chem.*, vol. 266, No. 26; 17640–17647 (1991).

Schwartz, S., et al., "The Intima. Soil for Atherosclerosis and Restenosis," *Circ. Res.*, vol. 77, No. 3; 445–465 (Sep. 1995).

Schwartz, R.S., et al., "Artery Size, Neointima, and Remodeling," *JACC*, vol. 32, No. 7; 2087–2094 (Dec. 1998).

Shi, Y., et al., "Origin of Extracellular Matrix Synthesis During Coronary Repair," *Circulation*, vol. 95, No. 4; 997–1006 (Feb. 18, 1997).

Shi, Y., et al., "Adventitial Remodeling After Coronary Arterial Injury," *Circulation*, vol. 93:340–348 (1996).

Shi, Y., et al., "Adventitial Myofibroblasts Contribute to Neointimal Formation in Injured Porcine Coronary Arteries," *Circulation*, vol. 94, No. 7; 1655–1664 (Oct. 1, 1996).

Sobeh, M.S., et al., "Induction of Prevention of Intimal Hyperplasia by Photodynamic Therapy in the Porcine Model," *SPIE*, vol. 2395; 390–395 (1995).

Statius van Eps, R.G., et al., "Photodynamic Therapy Inhibits the Injury–Induced Fibrotic Response of Vascular Smooth Muscle Cells," *Eur. J. Vasc. Endovasc. Surg.*, vol. 18; 417–423 (Nov. 1999).

Statius van Eps. R.G., et al., "Photodynamic Therapy Inhibits Transforming Growth Factor $\beta$ Activity Associated with Vascular Smooth Muscle Cell Injury," *J. Vasc. Sur.*, vol. 25, No. 6; 1044–1053 (Jun. 1997).

Statius van Eps. R.G., et al., "Photodynamic Therapy Inactivates Cell–Associated Basic Fibroblast Growth Factor: a Silent Way of Vascular Smooth Muscle Cell Eradication," *Cardiovasc. Res.*, vol. 35; 334–340 (1997).

Statius van Eps. R.G., et al., "Photodynamic Therapy of Extracellular Matrix Stimulates Endothelial Cell Growth by Inactivation of Matrix–Associated Transforming Growth Factor–$\beta$," *Lab. Invest.*, vol. 76, No. 2; 257–266 (1997).

Teirstein, P.S., et al., "Two–Year Follow–up After Catheter–Based Radiotherapy to Inhibit Coronary Restenosis," *Circulation*, vol. 99; 243–247 (Jan. 19, 1999).

Tsilimbaris, M.K., et al., "Pthalocyanine Mediated Photodynamic Thrombosis of Experimental Corneal Neovascularization: Effect of Phthalocyanine Dose and Irradiation Onset Time on Vascular Occlusion Rate," *Lasers Surg. Med.*, vol. 15; 18–31 (1994).

Waksman, R., et al., "Effect of Intravascular Irradiation on Cell Proliferation. Apoptosis, and Vascular Remodeling After Balloon Overstretch Injury of Porcine Coronary Arteries," *Circulation*, vol. 96, No. 6; 1944–1952 (Sep. 16, 1997).

Wight, T.N., et al., "Selective Deposits of Versican in the Extracellular Matrix of Restenotic Lesions from Human Peripheral Arteries," *Amer. J. Path.*, vol. 151, No. 4; 963–973 (Oct. 1997).

* cited by examiner

SIGNIFICANCE OF DOSIMETRY IN PHOTODYNAMIC THERAPY OF INJURED ARTERIES

CROSS-REFERENCE TO RELATED APPLICATIONS

This application claims priority to U.S. Provisional Patent Application Nos. 60/157,409 and 60/157,325, both filed on Oct. 1, 1999, entitled "Significance of Dosimetry in Photodynamic Therapy of Injured Arteries" and "Photodynamic Therapy with Methylene Blue for Post-Interventional Vascular Wound Healing", respectively, by Glenn M. LaMuraglia, the contents of which are incorporated herein by reference.

STATEMENT REGARDING FEDERALLY SPONSORED RESEARCH

This research was sponsored in part by the National Institute of Health under grant number HL02583 and the Office of Naval Research under contract N00014-94-I-0927. The U.S. government therefore, may have certain rights to this invention.

FIELD OF THE INVENTION

This invention generally relates to the use of photodynamic therapy as a method to modulate the postintervention vascular injury healing response.

BACKGROUND OF THE INVENTION

Photodynamic therapy (PDT) is a technique in which wavelength-specific, visible light is applied to activate otherwise relatively nontoxic photosensitizer dyes (PS) to generate cytotoxic free-radicals. These PDT-generated free-radical moieties are thought to exert cytotoxic effects by lipid peroxidation of cellular membranes and organelles. Although initially developed for cancer therapy, there are a considerable number of recent experimental studies that examined PDT-mediated inhibition of intimal hyperplasia (IH) which is regarded as one important obstacle to a satisfactory long-term patency after invasive vascular procedures. Intimal hyperplasia originates from an injury to the blood vessel wall, resulting in luminal encroachment from cellular proliferation and matrix deposition. The biologic effects of PDT are strictly limited to the proximity of the PS molecules when they are light-activated, because the half-life of the free-radicals ranges in the area of microseconds. Since the necessary components for PDT-mediated effects include oxygen, PS, and light; the appropriate dosimetry, which is multifactorial, may be important for effective treatment.

The development of procedures to treat arterial occlusive disease represents an important area in the field of surgery. Besides vascular surgery, novel interventional techniques have been developed including balloon angioplasty, stent depolyment and atherectomy. However, restenosis remains the major obstacle to satisfactory long term patency after therapeutic interventions for the treatment of vascular disease. All forms of reconstruction, whether interventional or surgical, cause a degree of injury to the vessel wall, which result in a injury healing response. Intimal hyperplasia (IH) is defined as the early post-interventional migration of smooth muscle cells (SMC) and myofibroblasts into the subintimal space of the vessel, and leads to cell proliferation and the production of excessive amounts of matrix protein. Recent studies have shown that, in addition to IH through its production of a physical mass, changes can occur in arterial wall geometry. Defined as arterial remodeling, these changes can also play an important role by altering the artery circumference due to fibrotic contraction or compensatory dilatation. This process of arterial remodeling and the degree of IH together, determine whether and to what extent an artery will develop restenosis. Although the molecular basis of vascular postinterventional renarrowing is not fully understood, the development of restenotic lesions has been shown to involve the production of specific matrix molecules such as procollagen type I and the large chondroitin proteoglycan versican. These molecules modulate cell function (migration, proliferation), the activity of growth factors, and local concentrations of lipids in the vascular wall. Cell-matrix interactions may also provide the basis for constrictive remodeling, which resembles a similar phenomenon in a nonvascular injury response.

Among numerous mechanical and pharmacological approaches, several have been investigated to inhibit the occurrence of restenosis. However, only intravascular stents and ionizing irradiation have been proven to clinically reduce this process, however, they have not been without their own shortcomings such as restenosis and thrombosis and do not provide an adequate solution to the problem.

Therefore, a need exists for the treatment of IH and/or restenosis which addresses the limitations known within the art.

SUMMARY OF THE INVENTION

The present invention is directed to methods for modulating, e.g., preventing, inhibiting or minimizing, restenosis in a subject after the subject has had an intervention to reopen an obstructed blood vessel. This is performed by administering a therapeutically effective amount of a photosensitizer to the treated, injured site and irradiating this treated injured site with a therapeutically effective amount of light energy, such that restenosis in the subject is modulated. In preferred embodiments, the photosensitizer is benzoporphyrin-derivative monoacid ring at a concentration of 25 µg/ml and the energy is delivered by laser at about 690 nm with an energy value of about 100 J/cm$^2$. In another preferred embodiment, the photosensitizer is methylene blue (MB) at a concentration of about 250 µg/ml to about 300 µg/ml and the energy is delivered by laser at about 660 nm with an energy value of about 100 J/cm$^2$.

The present invention is also directed to methods for modulating, e.g., preventing, inhibiting or minimizing, intimal hyperplasia in a subject by administering a therapeutically effective amount of a photosensitizer to a therapeutically intervened site and irradiating the treated site with a therapeutically effective amount of light energy, such that intimal hyperplasia in the subject is modulated. Typically the subject is a mammal, e.g., a human, a mouse, a rat, a horse, a dog, or cat.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
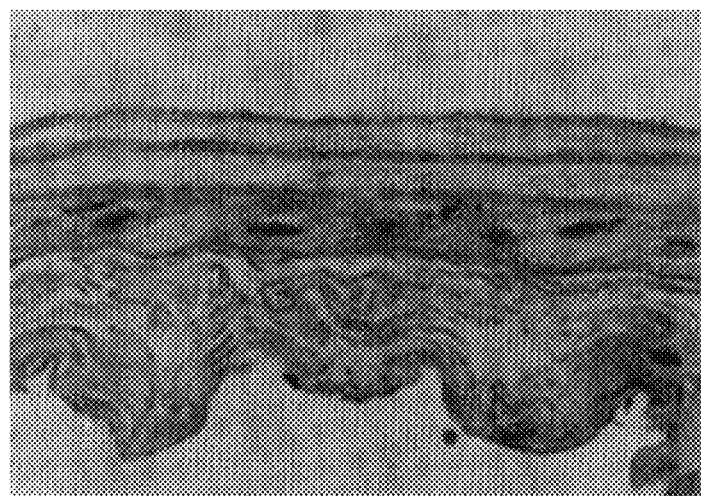
FIG. 1 is a photomicrograph of an arterial cross section, 24 hours following local delivery of 0.5 µg/ml BPD and irradiation with 50 J/cm$^2$ (Stage I)(Hematoxylin-eosin stain), Note: rare medial SMC and adventitial myofibroblasts.

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

The term "photodynamic" refers to the administration of a photosensitizing agent to a subject, including administration of a precursor of a photosensitizing agent, and subsequent irradiation with energy, e.g., light, of the target cells or tissue of the subject. It is believed that the photosensitizing agent preferentially accumulates in the target cells, because they are of an infective or damaged origin. It has now been surprisingly discovered that the administration of a photosensitizer, such as a BPD or MB, as a result of their morphology, causes the target cells or tissue contain relatively greater concentrations of light sensitive porphyrins, e.g., benzoporphyrin, and thus are more sensitive to light. Thus, the targeted tissue containing sufficiently high concentrations of the photosensitizing agent selectively absorb greater amounts of energy and can be selectively localized and distinguished from the adjacent cells or tissues. Photodynamic activation of the photosensitizing agent destroys the cells/tissue with increased concentrations of the photosensitizing agent. The effect of the light is dependent upon the photosensitizer selected wavelength or range of wavelengths, as well as the intensity and duration of administration of the energy, e.g., light. The preferred embodiment is to increase the concentration of the photosensitizing agent, e.g., MB or BPD, into the injury site of the intervention by direct and local application of the agent. This is advantageous in that the agent is concentrated locally at the injury site, and is not generally introduced systemically as it would dilute the concentration of the agent.

The term "photoactivation" is art recognized and is intended to mean a light-induced chemical reaction of a photosensitizer which produces a biological effect.

The term "photosensitizer" is art recognized and is intended to mean a chemical compound that produces a biological effect upon photoactivation or a biological precursor of a compound that produces a biological effect upon photoactivation.

The phrase "without tissue destruction" is intended to mean without formation of non-viable tissue that is lost as a result of necrosis or apoptosis leading to eschar formation and/or sloughing by the methods of the present invention. Tissue surrounding the treatment site is not damaged by the treatment methods of the invention. This is advantageous as the operator may not always be able to position as laser directly adjacent to the treatment site. This provides for a level of confidence that the site to be treated is treated (when in combination with PDT and a photosensitizer at a therapeutic concentration and at a therapeutic energy dose) and tissue not desirous of treatment is not.

Unless otherwise defined, all technical and scientific terms used herein have the meaning as commonly understood by one of ordinary skill in the art to which this invention pertains. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present document, including definitions, will control. Unless otherwise indicated, materials, methods, and examples described herein are illustrative only and not intended to be limiting.

The term "benzoporphyrin derivative" (BPD) is art recognized and is intended to include, for example, benzoporphyrin monoacid derivatives, tetracyanoethylene adducts of benzoporphyrin, dimethyl acetylenedicarboxylate adducts of benzoporphyrin, Diels-Adler adducts, and monoacid ring as a derivative of benzoporphyrin. Concentration of BPD useful in the present invention using local drug delivery ranges from about 0.5 µg/ml and about 250 µg/ml, preferably from about 1 µg/ml and about 100 µg/ml and most preferably from about 0.5 µg/ml and about 25 µg/ml. Systemic drug delivery will involve higher dose administration.

Methylene Blue (MB) is a clinical drug used clinically for staining purposes and for the treatment of methemoglobinemia. It is a photosensitizer, which has also been investigated for topical treatment in PDT. MB has a maximum light absorption at 660 nm, which allows deep and homogenous tissue penetration by light which is unaffected by blood. MB does not cause skin photosensitization to ambient light as other early photosensitizers. Concentration of MB useful in the present invention of local delivery ranges from about 0.1 µg/ml to about 1000 µg/ml, preferably from about 1 µg/ml and about 300 µg/ml and most preferably from about 250 µg/ml and about 300 µg/ml. Systemic drug delivery will involve higher dose administration.

It should be understood that as the drug concentration is increased in or about the treatment site, the less therapeutic light energy is required. Likewise, as the concentration of the drug is decreased, an increased dosage of therapeutic light is required. These parameters can be determined by those having ordinary skill in the art.

In one aspect, PDT has been found to inhibit restenosis. Photodynamic therapy (PDT) involves the excitation of a photo sensitizer which generates free radicals. These free radicals attack cell structure and can be used advantageously to promote the destruction of undesired cells. Various photo sensitizers such as phthelocyanine, can be used for this purpose. However it is unlikely phthelocyanine is a viable candidate for PDT treatments as it is unlikely that the FDA will approve its use for in vivo therapies. As an alternative, methylene blue is the photosensitizer of choice. Generally, it is not possible to use methylene blue for the purpose of IV administration, at least not easily, since the conversion to the leuko—form of methylene blue in serum is potentially problematic for penetration/adequate dosimetry regulation. However, methylene blue can be administered locally, as well as with either pressure or with the application of electrophoresis since the molecule is positively charged.

The detection of the intraarterial application of methylene blue or benzoporphyrin derivative is possible by using feedback fluorescence to determine the concentration of the dye in the arterial wall.

The methods of the invention can be applied to coronary applications, since coronary artery occlusion cannot be tolerated for an extended period of time. Two methods can be used to counteract distal ischemia. In one method, the balloon can remain fixed in position and gated to the cardiac cycle so that periods of deflation can occur to permit distal perfusion. This does not have to be per cardiac cycle and can be cycled as determined by the operator. In another method, balloon catheters can have holes in them. For instance, an outer balloon can be made with large holes in it from a longitudinal perspective (balloon within a balloon) such that blood can flow through the permeable balloon as the cardiac cycle repeats. The inner balloon can be inflated and deflated as necessary and used to position the light emitting device adjacent to the treatment site.

The present invention modulates, e.g., inhibits, restenosis and modulates vascular injury healing by using PDT with the local delivery of MB or BPD.

The PDT methods of the invention are surprising, in that other vascular PDT studies could not achieve inhibition of IH with PDT, in fact, PDT appeared to accelerate the development of stenotic lesions. The present invention provides the unexpected result that specific combinations of PDT, photosensitizer and energy can modulate, e.g., inhibit, IH and/or restenosis in a subject. Not to be bound by theory, it is believed that the conflicting data with reference to the ability of PDT to inhibit IH in injured arteries, may be based not only on the use of divergent protocols, animal models, and vessel sizes; but on the different photosensitizers and light dosimetry employed. Thus, the present invention provides specific combinations of PDT, photosensitizer, and energy requirements for immediate and short-term biologic responses in the artery wall after PDT using varying concentrations of photosensitizer and light fluences to systematically define its effect on the development of IH.

With conflicting results in the literature on the ability of PDT to inhibit intimal hyperplasia (IH), the present invention provides for therapeutic effects of drug and light dosimetry on the biologic responses in the artery wall.

To demonstrate the efficacy of the methods of the invention, rat common carotid artery was balloon-injured and pressurized with benzoporphyrin-derivative monoacid ring (BPD). The rat model is an accepted model predictive for human therapy. PDT was performed with external laser at different fluences and biologic responses of the artery wall were histologically examined at 24 hours and at 2 weeks. The application of external laser is not considered limiting. In an alternative embodiment, light energy would be delivered by use of a balloon so that it is applied internally. A combination of both external and internal therapeutic energy is also within the scope of the invention.

Photodynamic therapy effects on injured arteries were classified into four stages. For example, low dose PDT using 0.5 µg/ml BPD at 50 J/cm$^2$ (stage I) resulted in incomplete cell eradication and significant IH at 2 weeks. Irradiation with 100 J/cm$^2$ at the same BPD concentration (stage II), completely eradicated the cells in the artery wall at 24 hours, but still led to IH at 2 weeks. However, 25 µg/ml BPD at 100 J/cm$^2$ (stage III) resulted in total cell eradication at 24 hours and inhibition of IH at 2 weeks. In contrast, high dose PDT with 25 µg/ml BPD and 200 J/cm$^2$ (stage IV) led to thrombus development and vascular occlusion at 24 hours.

The invention demonstrates the different stages of PDT effects on injured arteries and emphasizes the critical importance of appropriate PDT dosimetry for the effective inhibition of IH. Unlike previous studies, the present invention provides a predictable method for the treatment of IH and/or restenosis and is applicable for other photosensitizers such as MB.

The present invention is directed to methods for modulating, e.g., preventing, inhibiting or minimizing, restenosis in a subject by administering a therapeutically effective amount of a photosensitizer to a vascular therapeutic site and irradiating the treated vascular site of injury with a therapeutically effective amount of light energy, such that restenosis in the subject is modulated. In preferred embodiments, the photosensitizer is BPD at a concentration of about 25 µg/ml and the energy is delivered by laser at about 690 nm with an energy value of about 100 J/cm$^2$.

The present invention is also directed to methods for modulating, e.g., preventing, inhibiting or minimizing, intimal hyperplasia in a subject by administering a therapeutically effective amount of a photosensitizer to a vascular therapeutic site and irradiating the treated injury site at about 690 nm with BPD or 660 nm with MB with a therapeutically effective amount of light energy, such that intimal hyperplasia in the subject is modulated.

The term "modulate" is intended to mean an intervention or treatment that results in the reduction in IH and/or restenosis and/or arterial remodeling relative to an untreated subject suffering from similar intervention to vascular architecture. The reduction of the injury response to the subject's tissue can be complete, e.g., inhibited, or at least minimized relative to an untreated subject. In certain aspects, the trauma can be prevented by the methods of the invention.

The term "subject" is intended to include mammals, such as humans, mice, rats, sheep, cows, cat, dogs, and horses.

The phrase "therapeutically effective amount" is that amount of a therapeutic compound, e.g., a photosensitizer, preferably BPD or MB, necessary or sufficient to perform its intended function within a subject at a given wavelength, e.g., 690 nm for BPD or 660 nm for MB, during a period application, e.g., treat or prevent restenosis, IH, arterial remodeling in subject. An effective amount of the therapeutic compound can vary according to factors such as the amount of the causative agent already present in the subject, the age, sex, and weight of the subject, and the ability of the therapeutic compounds of the present invention to affect photosensitization in the subject. It has been discovered that the photosensitizer is selectively adsorbed/absorbed by the treatment tissue. This morphological characteristic is not completely understood, however, the damaged tissue site acts to provide increased concentration levels of the photosensitizer for treatment in comparison to surrounding undamaged tissue.

One of ordinary skill in the art would be able to study the aforementioned factors and make a determination regarding the effective amount of the therapeutic compound without undue experimentation. An in vitro or in vivo assay also can be used to determine an "effective amount" of therapeutic photosensitizers such as BPD. The ordinarily skilled artisan would select an appropriate amount of the therapeutic compound for use in the aforementioned assay or as a therapeutic treatment. A preferred concentration range for BPD is between about 0.5 $\mu$g/ml to about 50 $\mu$g/ml, preferably between about 0.5 $\mu$g/ml and about 25 $\mu$g/ml, most preferably about 25 $\mu$g/ml. A preferred range for irradiation is between about 50 J/cm$^2$ and about 200 J/cm$^2$, preferably about 100 J/cm$^2$. A preferred combination of BPD and irradiation is between about 0.5 $\mu$g/ml at 50 J/cm$^2$ and about 25 $\mu$g/ml at 200 J/cm$^2$.

One of ordinary skill in the art would be also be able to study the aforementioned factors and make a determination regarding an effective amount of MB without undue experimentation. An in vitro or in vivo assay also can be used to determine an "effective amount" of MB. The ordinarily skilled artisan would select an appropriate amount of MB for use in the aforementioned assay or as a therapeutic treatment. A preferred concentration range for MB is between about 0.5 $\mu$g/ml to about 800 $\mu$g/ml, preferably between about 0.5 $\mu$g/ml and about 250 $\mu$g/ml, most preferably about 250 and about 300 $\mu$g/ml. A preferred range for irradiation is between about 10 J/cm$^2$ and about 1000 J/cm$^2$, preferably about 100 J/cm$^2$. A preferred combination of MB and irradiation is between about 250 $\mu$g/ml at 50 to about 100 J/cm$^2$, i.e., 50 J/cm$^2$, and about 300 $\mu$g/ml at 200 to about 300 J/cm$^2$, i.e., 200 J/cm$^2$.

A preferred range for the delivery of phototherapeutic energy, e.g., PDT, is in the range where the wavelength energetically excites the drug. Generally, this range is in the visible to near infrared and is from about 350 nm to about 900 nm, for example, from about 600 and about 700 nm to avoid blood absorption, preferably between about 625 nm and about 690 nm, and most preferably about 690 nm for BPD and about 660 nm for MB.

Although lasers are preferred for the delivery of phototherapeutic light, any high energy light source is useful for the methods of the invention. Suitable high energy light sources can also include xenon light, halogen light, arc light sources, but preferably those that can be transmitted through fiberoptic. These are generally used to treat the artery using intralumenal irradiation so that the photodynamic therapy can be administered (both photosensitizer drug and light) to the area of interest from a remote access site to the area of blood vessel of interest. However, it could be applied by either photosensitizer drug or light delivery in a systemic fashion to affect only the area of interest.

A therapeutically effective treatment preferably diminishes at least one symptom or effect associated with trauma to the blood vessel by at least about 20%, more preferably by at least about 40%, even more preferably by at least about 60%, and still more preferably by at least about 90–100% relative to untreated subjects. Assays can be designed by one skilled in the art to measure the diminishment of such symptoms and/or effects. Any art recognized assay capable of measuring such parameters is intended to be included as part of this invention.

The therapeutic intervention site can be an injury site. Typically, the injury site in a blood vessel or artery is from an intervention to the tissue by a foreign object. In general, this injury is most often caused by those methods known in the art which are used to repair veins and arteries and/or to remove plaque from the same. For example, the wound or injury site can be caused by common procedures or interventions by stents, balloon angioplasty, endarterectomy or atherectomy procedures. This list in not limiting and one skilled in the art would recognize other common procedures or tools used in interventions or surgical procedures which can cause injury to veins and arteries such that restenosis or IH occurs.

Photodynamic therapy is a treatment that utilizes photosensitizing drugs activated by light to induce cytotoxicity and effects to the extracellular matrix. It has been used for neoplastic and non-neoplastic applications with several thousand patients having undergone PDT in the last 15 years. For example, the in vivo tissue response to PDT of tumors is characterized by a rapid onset of vascular thrombosis (photothrombosis), hemorrhage, inflammation, and both direct and hypoxia-induced cell death. In contrast, PDT of larger vessels, despite comparable light and drug dosimetry, usually initiates a favorable vascular healing response without causing thrombosis.

The present invention provides that microscopic assessment of balloon-injured arteries subjected to the "proper" PDT dosimetry demonstrates an absence of inflammation or aneurysmal dilatation, an inhibition of experimental IH, and a rapid repopulation of the adventitia with myofibroblasts and of the intima with endothelial cells. Following PDT of large vessels, there is minimal repopulation of the media with smooth muscle cells and no increased cellular proliferation or migration at the boundary between PDT-treated and untreated artery.

It is also a paradox that using the "proper" PDT parameters of large vessels, while leading to complete eradication of cells in the vessel wall, does not elicit the same biologic response as other forms of vascular wall injury such as balloon injury, thermoablative laser irradiation, and surgery. Moreover, it has not been not clear why an additional injury from PDT after the initial balloon injury results in a less reactive response. Combined balloon injury, pressure- and PDT-related injury to the vascular wall, which may precipitate structural destabilization of the artery, were previously studied. In that study, light microscopy of saline-pressurized arteries at 21 days indicated the presence of additional injury to the media with eradication of smooth muscle cells and a statistically significant decrease of medial thickness compared to only balloon injury. When PDT followed the pressure injury to the artery, a small diameter increase was noted at 21 days. However, the mechanical integrity of arteries following PDT was not found to be different. Besides balloon injury and local BPD pressurization, PDT represented an additional injury (prior to the present invention), which could also be associated with the release of growth factors and the prevalence of a large number of proliferating cells. Since no such observation and no inflammatory response were noted in the present invention, the present PDT therapy not only eliminated the entire population of vessel wall cells, but also modified the extracellular matrix, which is known to contain biologically active molecules.

The data provided by the present invention, demonstrates the surprising result that a very low dose of PDT results in incomplete cell eradication of the targeted vessel segment and causes significant IH within 2 weeks. On the other hand, a very high PDT dose results in thrombosis and vascular occlusion comparable to the findings in tumor vessels and neovascularization. Hence, following the escalating PDT-dosimetry and the observed histologic changes demonstrated by the present invention, four stages of biologic responses to vascular PDT can be outlined (Table 2) and can be utilized for the therapeutic treatment of vessels or arteries.

Figure 2:
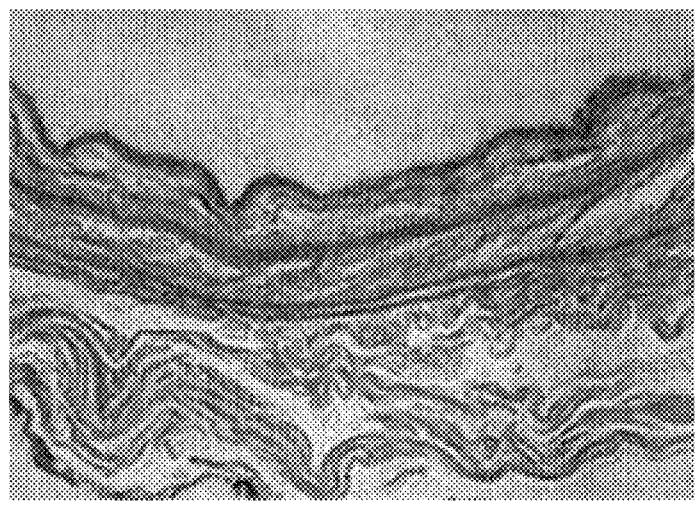
FIG. 2 is a photomicrograph of an arterial cross section, 24 hours following local delivery of 0.5 µg/ml BPD and irradiation with 100 J/cm² (Stage II)(Hematoxylin-eosin), Note: completely acellular intima and media and single leukocyte in the periadventitia.
Figure 4:
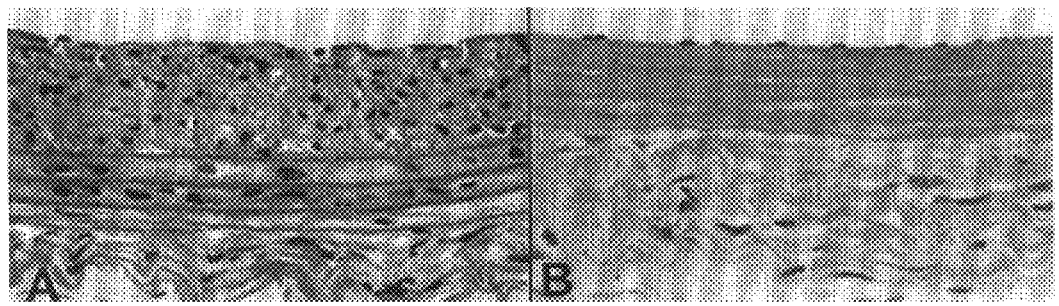
FIG. 4A is an arterial cross section, (Stage II), 2 weeks following PDT (Hematoxylin-eosin), Note: significant IH.
FIG. 4B is an arterial cross section (Stage III), 2 weeks following PDT (Hematoxylin-eosin), Note: Lining of the luminal surface with a monolayer of flat cells (The media presents acellular. In the adventitia there is population with fibroblasts with no evidence for inflammation).

The present invention demonstrates, surprisingly, for the first time that in accordance with in vitro findings the effect of PDT in vivo does not uniquely relate to its well-known cytotoxic potential. Although, the entire cell population of the arterial wall was eliminated in stages II to IV, the impact of PDT on the biologic outcome at these stages was completely different. At stage II there was induction of significant IH, at stage III inhibition of an inflammatory response and prevention of IH, while at stage IV photothrombosis was noted. These observations provide that besides induction of cytotoxicity, a dose-dependent alteration of the extracellular environment also occurs in vivo. A previous in vitro study has shown that the threshold dose for PDT-mediated cytotoxicity was lower than for bFGF inactivation. This in vitro observation also concurs with the mitogenic response of smooth muscle cells in vivo. The combined observations of the present invention provide that cells, which survive sublethal PDT at low drug and light dosimetry (group 1), grow in an environment, which is enriched with growth factors and cytokines and may therefore develop exuberant IH (Stage I). Moreover, the in vitro data correspond with the findings in group 2 of the present invention. Although drug and light dosimetry in group 2 passed the cytotoxicity threshold and resulted in complete cell eradication of the arterial wall, (FIG. 2) bFGF could still be detected in all layers of the vascular wall. It was also noted at two weeks following PDT, the intimal thickness in group 2 was significantly increased (FIG. 4a).

Figure 5:
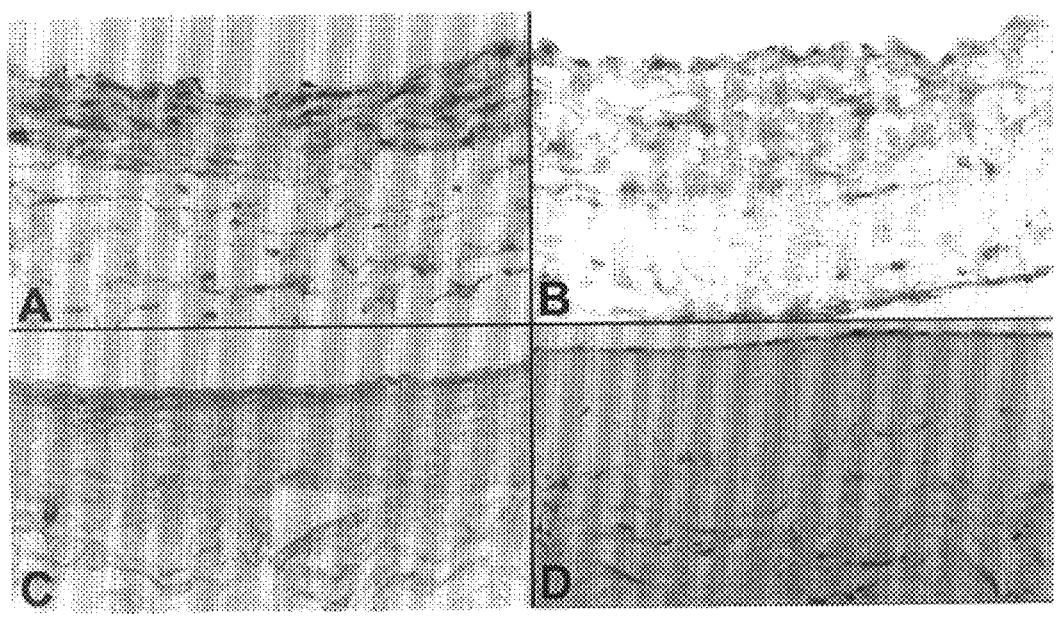
FIG. 5A is an arterial cross-section of a normal artery with immunohistochemistry staining for bFGF, evidence of bFGF in all layers of the vascular wall.
FIG. 5B is an arterial cross-section 24 hours following PDT (Stage II) with immunohistochemistry staining for bFGF, evidence of bFGF in all layers of the vascular wall.
FIG. 5C is an arterial cross-section 24 hours following PDT (Stage III) with immunohistochemistry staining for bFGF (brown), and counterstained with nuclear fast red, Note: Luminal layers of the media demonstrate faint brown staining, whereas all other layers are negative for bFGF.
FIG. 5D is an arterial cross-section at two weeks following PDT (Stage III) with immunohistochemistry for bFGF, evidence for bFGF in the flat cells, presumably endothelial cells, at the luminal surface.

The presence of biologically active growth factors and cytokines is critical for vascular remodeling. It is indicated that wound fibroblasts and cells in the periadventitial tissue have the potential to migrate into the vascular wall, transform into myofibroblasts and induce IH. Ineffective elimination of growth factors and cytokines in the vessel wall can have induced the chemoattraction, migration and proliferation of myofibroblasts in the immediate environment of the targeted blood vessel. Therefore, eradication of both effector cells of IH and mitogens in the extracellular matrix, is imperative for the success of PDT to inhibit IH. In fact, the immunohistochemistry demonstrated that bFGF was entirely eliminated from the vascular wall following optimal PDT dosimetry (group 3) (FIG. 5B), whereas specimens from group 2 clearly demonstrated positive staining for bFGF in all layers of the vascular wall (FIG. 5a). As a consequence, the present invention provides a therapeutic window in which PDT can inhibit the development of IH. Prior to this invention, it was found that four important factors may determine the biologic response of blood vessels to PDT: light dosimetry, drug dosimetry, photosensitizer partitioning, and vessel size. However, none of these studies found what the critical parameters were to effect therapeutic treatment. The present invention provides that increasing laser fluence generated more vascular injury at comparable tissue photosensitizer concentrations.

Moreover, additional experiments indicated that similar biologic responses in the artery wall can be attained with increasing photosensitizer doses and simultaneously reducing laser light irradiation. In a previous study, irradiation of targeted corneal vessels at two different time points after phthalocyanine injection resulted in statistically significant increase of the light dose necessary to induce thrombosis. In that study, a statistically significant difference was also found in the irradiation time necessary to achieve vascular occlusion using five different phthalocyanine doses between 3 and 14 mg/kg indicating a possible linear correlation between dose of phthalocyanine and irradiation time.

Vascular PDT can be performed safely and efficiently with local or systemic drug delivery and systemic or endoluminal light irradiation. What the present invention provides, is the appropriate drug and light dose at different sites and different layers of the vascular wall. It has been suggested that the adventitia plays a more important role in restenosis than previously thought. Therefore, external irradiation may appear more meaningful. On the other hand, endoluminal delivery of light via an appropriate balloon is more practical for patients.

Since PDT-effects can only occur where photons interact with drug molecules, light distribution, dosimetry, partitioning and tissue concentration of the photosensitizer in the vascular wall ultimately determine the site and extent of the tissue damage. Others suggested that the major determinant for vascular photosensitivity in all cases might be the level of circulating photosensitizer. As blood levels fall, vascular occlusion is less likely. The present invention, in which localized photosensitizer delivery was deliberately chosen in order to keep circulating drug levels as low as possible, provides that it is not the blood concentration of the photosensitizing compound by itself, but rather the tissue concentration that appears to be more important.

In summary, the conflicting data on PDT effects to developing IH in injured arteries prior to this invention, can now be explained by inadequate dosimetry of drug and light with respect to the targeted tissue and the model used. Thrombosis occurs at high PDT doses. In the vascular system this therapeutic modality can no longer be regarded as a simple tool to eradicate cells, but as a catalyst for the initiation of a favorable vascular healing response which proves to be imperative for its successful inhibition of restenosis. In this context, adequate PDT-dosimetry which takes into account the properties and peculiarities of the photosensitizer, the light dosimetry, and the targeted vessel, is needed to achieve the desired biologic response. Therefore, the use of a classifying score as provided by the present invention can help to categorize and better interpret the sequelae of any PDT treatment designed to prevent the development of vascular restenosis.

The invention is further illustrated by the following examples which in no way should be construed as being further limiting. The contents of all references, pending patent applications and published patent applications, cited throughout this application, including those referenced in the background section, are hereby incorporated by reference. It should be understood that the models used throughout the examples are accepted models predictive of efficacy in humans.

Materials and Methods

Male Sprague Dawley rats (Charles River Breeding Laboratories, Wilmington, Mass.), weighing 350–450 g, were anesthetized with intramuscular Ketamine (75 mg/kg), Xylazine (5 mg/kg), and Atropine (40 $\mu$g/kg). A midline neck incision was performed and the left carotid artery was exposed. After clamping the common carotid and the internal carotid artery, a 2 F (French Fogarty embolectomy catheter (Baxter Health Care Corporation, LIS Division, Irvine, Calif.) was introduced into the common carotid artery via the external carotid artery. The common carotid artery was subsequently injured by inflating the balloon with 0.2 ml air and gently passing and rotating the catheter three times.

After balloon-injury, a 22 gauge polyethylene catheter was advanced through the external carotid arteriotomy into the distal portion of the common carotid artery and secured with a suture. The catheter was connected via three-way stopcock to a Statham transducer for synchronous pressure monitoring with a digital pressure manometer (HP 78205C, Hewlett Packard, Palo Alto, Calif.). The second generation photosensitizer benzoporphyrin-derivative monoacidic ring (BPD-MA Verteporfine®, Quadra Logic Technologies Inc., Vancouver, BC, Canada), provided as a liposomal preparation, was reconstituted in distilled water (2 mg/ml) and diluted in physiologic saline to a final concentration of 25 $\mu$g/ml. Once the arterial segment was isolated with microclamps under low ambient light, BPD was delivered at a pressure of 400 mm Hg for two minutes. Previous fluorescence microscopy studies have shown that using this protocol, 15 minutes following delivery of BPD, photosensitizer fluorescence could be detected through the entire arterial wall. The highest intensity was seen in the medial layers closest to the lumen, whereas a relatively weak signal was obtained from the adventitia. Following aspiration of BPD from the arterial lumen, the artery was flushed with saline, the catheter was removed, and blood flow was restored to the internal carotid artery.

Photodynamic Therapy. Fifteen minutes following delivery of the PS to the artery wall, the common carotid artery was externally irradiated as previously described. Briefly, an argon-pumped dye laser (Coherent Innova I 100 and Coherent CR 599, Coherent, Palo Alto, Calif.) was tuned to 690 nm light at an irradiance of 100 mW/cm$^2$, coupled to a 600 $\mu$m optical fiber, and using a 5-mm focal length lens magnified to obtain a uniform 2-cm spot. The targeted artery was submerged in physiologic saline, placed on a right-angled reflective mirror, and optically isolated with black, light-impervious tape. All procedures were approved by an independent institutional animal care committee. Animal care complied with the "Principles of Laboratory Animal Care" and the "Guide for the Care and Use of Laboratory Animals" (NIH Publication No. 80/23, revised 1985).

Experimental groups. The arteries were assigned to four different experimental groups: group 1 (n=6) and 2 (n=6) consisted of arteries which were pressurized with 0.5 $\mu$g/ml BPD and irradiated at a fluence of 50 and 100 J/cm$^2$ respectively. Group 3 (n=15) and 4 (n=4) were pressurized with 25 $\mu$g/ml BPD and irradiated at 100 or 200 J/cm$^2$ respectively.

Harvest. The animals were sacrificed 24 hours and 2 weeks after PDT. The carotid artery was flushed with saline. They were either in situ perfusion-fixed at 80 mm Hg with 10% buffered formalin for light microscopy or rinsed with saline, embedded in Tissue tek O.C.T. compound® (Miles Inc. Elkhart, IN) and stored at −70° C. for immunohistochemistry.

Histology. For each animal, the harvested artery was processed into three segments: proximal, mid, and distal. Multiple five-$\mu$m thick cross-sections were prepared from each specimen of the artery, and a representative from each segment was analyzed. All paraffin-embedded specimens were stained with hematoxylin and eosin. Arterial diameters, as delineated by the length of the internal elastic lamina (IEL circumference=$\pi$d), as well as intimal—and medial areas were measured using morphometric analysis with a camera lucida digitizing measurement system as previously described (Sigma Scan, Jandel Scientific, San Rafael, Calif.).

Immunohistochemistry. Immunohistochemistry for basic fibroblast growth factor (bFGF) was undertaken to verify possible differential, dose-dependent effects on this growth factor which resides in the vascular wall and is known to play an important role in the early development of IH in rats. Monoclonal antibody to bFGF (Zymogenetics, Seattle, Wash.) was used to verify the presence of bFGF in the specimens using the two-layer indirect immunoperoxidase technique previously described. Briefly, the primary antibody (1:1000) was labeled by biotinylated horse anti-mouse immunoglobulin (Vector Laboratories, Burlingame, Calif.) and counterstained with nuclear fast red (Sigma Chemical Co., St. Louis, Mo.). Normal arteries were used as positive control, and arteries stained with a nonspecific primary antibody were used as negative controls to exclude nonspecific binding by the primary or secondary antibody.

Statistics. All data is expressed as mean ± standard deviation. Data comparison was performed with a single factor ANOVA using a commercially available statistics software package (Statistica 5.0, Statsoft, Tulsa, Okla.). P values of less than 0.05 were considered significant.

Results

At harvest, all animals appeared healthy without evidence of weight loss or wound infection. Animals subjected to BPD developed no signs of systemic phototoxicity.

Figure 3:
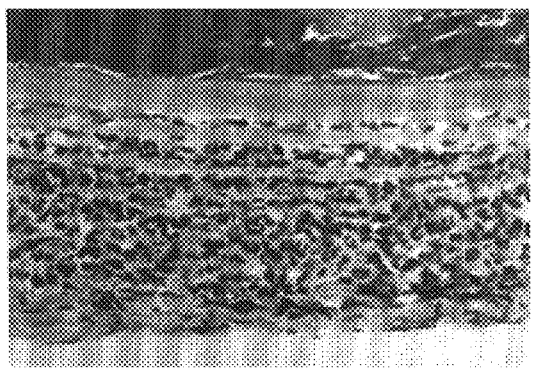
FIG. 3 is an arterial cross section 24 hours following local delivery of 25 µg/ml BPD and irradiation with 690 nm laser light at 200 J/cm² (Stage IV)(Hematoxylin-eosin), thrombosis of the vessel lumen, complete necrosis of the media with cellular debris, massive inflammatory reaction with invasion of mononuclear cells into the adventitia.

Light microscopy and morphometric analyses. In groups 1, 2 and 3 the arterial specimens demonstrated no signs of inflammation or thrombosis 24 hours following PDT. The examined segments revealed a denuded luminal surface without evidence for platelet adhesion, microthrombi, or inflammation. In group 1, the media and the adventitia demonstrated a small number of smooth muscle cells and fibroblasts (FIG. 1). Cross sections of arteries in group 2 (FIG. 2) and 3 were entirely cell-free. Following high dose PDT with local delivery of 25 $\mu$g/ml BPD and irradiation with 200 J/cm$^2$, thrombosis and occlusion of the entire vessel lumen was observed at 24 hours (FIG. 3). The media was devoid of smooth muscle cells with the spaces between the laminae slightly diminished and filled with amorphous matrix. In the adventitia a severe inflammatory reaction with infiltration of both polymorphonuclear and mononuclear cells was noted.

At two weeks, histology of arterial cross sections demonstrated formation of unevenly distributed IH in group 1

(0.18±0.03 mm$^2$) and group 2 (0.14±0.03 mm$^2$; FIG. 4a). Histology of arterial specimens in group 3 demonstrated an occasional area of cells in the intima with a statistically significant smaller intimal area (p<0.001) (FIG. 4B). These arteries presented with a denuded luminal surface without evidence of gross platelet adhesion, microthrombi, inflammation, or intimal thickening. The areas of IH in group 3 were associated with the distal or proximal ends of the treated segment.

The medial areas and diameters in group 1 and 2 were almost identical (Table 1), while in group 3 arteries presented with a significantly thinner media (p<0.003). The media in group 3 was devoid of smooth muscle cells with the spaces between the laminae slightly diminished and filled with amorphous extracellular matrix, while in group 1 and 2 normal repopulating smooth muscle cells were detected. The diameter of the arteries did not show statistically significant differences between the four groups.

Immunohistochemistry. Immunohistochemical staining to bFGF of separate balloon-injured control arteries in a pilot study (n=4) demonstrated positive staining and irregular positive clumping of the media but little to no staining of the adventitia (FIG. 5a). The specimens that were exposed to nonspecific primary antibody (negative control) only displayed counterstaining with nuclear-fast red. Immunohistochemical analysis of arteries in group 2 (FIG. 5B) showed avid brown staining in all layers of the vascular wall without evidence for cell nuclei in the intima and the media, but for rare cells in the adventitia. On the other hand, cross sections of arteries from group 3 demonstrated a slight staining of the inner elastic lamina, 24 hours after PDT (FIG. 5c). There was no evidence of bFGF staining in the media or adventitia. After two weeks there was positive bFGF staining only of endothelial cells in the intima and fibroblasts in the adventitia. (FIG. 5d).

TABLE 1

Morphometric Data at 2 weeks

| Groups | Intimal Area (mm$^2$) | Medial Area (mm$^2$) | Diameter (mm) |
| --- | --- | --- | --- |
| 1 (n = 6) | 0.18 ± 0.03 | 0.18 ± 0.01 | 0.93 ± 0.02 |
| 2 (n = 6) | 0.14 ± 0.03 | 0.18 ± 0.05 | 0.95 ± 0.06 |
| 3 (n = 15) | 0.01 ± 0.01*‡ | 0.10 ± 0.02† | 0.82 ± 0.04 |
| 4 (n = 4) | — | 0.17 ± 0.01 | 0.91 ± 0.03 |

Mean ± standard deviation; *p < 0.001 versus 1 and 2 (ANOVA); †p < 0.003 versus 1 and 2; ‡IH developed only in the distal and proximal sections near clamp site

TABLE 2

Biologic Responses to Vascular PDT

| | Cells | Mitogens | Inflammation | IH |
| --- | --- | --- | --- | --- |
| Stage I | ++ | +++ | − | +++ |
| Stage II | − | ++ | − | +++ |
| Stage III | − | −(+) | − | − |
| Stage IV | − | +++ | +++ | −* | cells = presence of effector cells of intimal hyperplasia (IH); mitogens = presence of basic fibroblast growth factor in the vessel wall; inflammation = presence of inflammatory cells in the vessel wall; *Acute thrombosis Methylene Blue Studies Methods: Rat carotid arteries were balloon-injured (BI), the photosensitizer methylene blue (MB) was delivered locally, and the arteries irradiated with thermoneutral laser light ($\lambda$=660 nm, 100 J/cm$^2$). Control animals included BI along and MB after BI alone. Arteries were analyzed after 2 weeks with morphometric evaluation (per group: n=6), and in situ hybridization for versican and pro-collagen type 1 gene expression (digitized image pixel analyses, n=9).

Results: PDT-treated arteries developed no IH (0±0 mm$^2$, compared to BI: 0.192±0.006 mm$^2$ P<0.0001). The vascular geometry did not change significantly (Diameter: PDT: 0.95±0.04 mm, BI: 0.94±0.05 mm, untreated contralateral carotid artery: 0.91+0.06 mm). Arterial injury resulted in an increase of versican and pro-collagen type I mRNA in the adventitia and the neointima. In the repopulating cells of the adventitia after PDT, there was a significant decrease in versican mRNA (% of positive pixels per high power field: PDT: 1.11±0.37%, BI: 2.94±0.58%, P<0.01) but not in pro-collagen type I mRNA.

Conclusion: Site-specific delivery of MB, a clinically appropriate photosensitizer, followed by PDT represents a suitable method to promote favorable healing of arteries after trauma to vascular structures, e.g., balloon intervention. The decrease of versican mRNA expression of cells repopulating after PDT confirms the effect PDT has on healing and further supports its role for inhibiting post-interventional restenosis.

Materials and Methods

Experimental Design: Male Sprague Dawley rats (Charles River Breeding Laboratories, Wilmington, Mass.) weighing 350–420 g, were anesthetized with intraperitoneal Ketamine (50 mg/kg), Xylazine 5 mg/kg) and Atropine (40 $\mu$g/kg). Common carotid artery balloon injury was performed using a 2-French Fogarty embolectomy catheter (Baxter Health Care Corporation, Edwards Division, Irvine, Calif.). After balloon-injury, a 22-Gauge polyethylene catheter was advanced through the external carotid artery into the common carotid artery, which was isolated with micro clamps. In brief, the balloon was introduced into the common carotid artery and inflated with 0.65 mL of air. After three passages, the embolectomy catheter was removed, an da 22-gauge polyethylene catheter was advanced through the external carotid artery into the common carotid artery, which was isolated with microclamps. The catheter was connected via a three-way stopcock to a Stratham transducer for synchronous pressure monitoring (HP 78205C, Hewlett Packard, Mass.). Methylene blue (American Regent Laboratories, Shirley, N.Y.), was diluted in 5% Dextrose and Lactated Ringer's solution (Abbott Laboratories, Chicago, Ill.) and pilot studies (data not included) indicated a final concentration of 250 $\mu$g/ml to be optimal for PDT. Under low ambient light, the drug was injected into the common carotid artery with 180 mm HG for 2 minutes. After local delivery, MB was aspirated from the arterial lumen, the artery was flushed with saline and the catheter removed. The external carotid artery was ligated, and the blood flow was restored.

The animals were randomly assigned to the following 3 groups: Group PDT (n=6): balloon injury followed by application of photosensitizer and laser irradiation; Group PS (n=6): balloon injury followed by the photosensitizer MB application alone; Group BI (n=6): no treatment other than balloon-injury (BI) to the carotid artery.

Since laser light irradiation alone does not change the vascular injury response in this model, this group was not included.

Animals had free access to a standard rat chow (Purina rat chow 5001, Ralson Purina, St. Louis, Mo.) and water while maintained in a standard 12-hour light/dark cycle. An independent institutional animal care committee approved all procedures. Animal care complied with the "Principles of Laboratory Animal Care" and the "Guide for the Care and Use of Laboratory Animals" Institute of Laboratory Animal Resources, Commission on Life Sciences, National Research Council, Washington National Academy Press, 1996.

MB localization studies: Three animals were used to determine the MB photosensitizer distribution in the arterial wall. The animals were sacrificed 5 minutes after BI and local MB delivery to the left carotid artery as described. The arterial system was flushed with saline, and the carotid arteries were excised, embedded in tissue tek O C T compound™ (Miles Elkhart, Ind.), and stored at −70° C. Five-$\mu$m-thick cross sections were covered with PBS and the distribution of MB in the artery wall was determined using a confocal microscope (TCS NT, Leica, Wetzlar, Germany). Digital images were captured using an excitation of 476 nm, and emission between 620 and 630 nm. The contralateral, non-photosensitizer impregnated carotid artery served as a negative control.

Photodynamic Therapy: Five minutes after local delivery of MB, the common carotid artery was externally irradiated with 660 nm laser light, emitted by a diode laser (Alto-Surgeon SRG-3, Polaroid, Cambridge, Mass.) to deliver a total fluence of 100 J/cm$^2$ at an irradiance of 100 mW/cm$^2$. The diode laser was coupled to a 600-$\mu$m optical fiber through a microlens to obtain a uniform 1-cm spot. The targeted artery was submerged in 0.9% saline and placed on a right-angled reflective mirror to achieve uniform irradiation, as previously described. The irradiated vessel segment was marked with periadventitial India ink.

Harvest: Animals were sacrificed 14 days after surgery by an overdose of pentobarbital. Following sacrifice, the iliac artery was cannulated and the arterial system was flushed with saline and in situ perfusion-fixed at 150 mm Hg with 10% buffered formalin. The balloon-injured vessel segments and the contralateral carotid artery were excised and placed in fresh 10% buffered formalin. After embedding in paraffin, multiple 4 $\mu$m thick cross sections were obtained from the proximal, mid, and distal vessel segments.

Vessel Histomorphometry: The histologic analyses of the arteries stained with hematoxylin and eosin consisted of both a descriptive and quantitative morphometric evaluation. The morphometry of the arteries was measured using a digitizing measurement system (Color CCB Camera Model 2222-1010, COHU Inc., San Diego, Calif.) and analyzed using the Scion Image software (Scion Corporation, Frederick, MY). Intimal area, medial area, and vessel diameter, as delineated by the external elastic lamina, were measured and calculated as previously described. In addition, adventitial cells were counted manually and are expressed as the number of cells per high power microscopic field (×400). Because the area of the adventitia varies within the different specimens, high power fields were used for all quantitative measurements of adventitial cell numbers and gene expression in the in situ hybridization experiments.

Digoxigenin in situ hybridization: Groups for in situ hybridization included PDT, BI, and the uninjured contralateral artery (n=3). Because no differences between the BI and PS groups were revealed by means of histologic and morphometric analyses, which provided no MB-induced modulation of the vascular injury healing response, the PS group was not included in the in situ hybridization experiments. Complementary DNAs (cDNAs) for type I procollagen and versican core protein were obtained as PCR fragments with each gene specific primers in which reverse primers contain T7 RNA polymerase recognition sequence at their 5' end. Primer sequences were as follows. For pro-collagen type I: TGACTTCAGCTTCCTGCCTCAGCC (SEQ ID: 1) and TAATACGACTCACTATAGGGAGGCCCTG-GAGGAGCAGGGCCTTCTTG (SEQ ID: 2) (Li SW et al. Matrix Biol. 1995, 14:593–595). For versican: GGAGAC-GACTGTCTTGGTGGCCCAG (SEQ ID: 3) and TAATAC-GACTCACTATAGGGAGGACAGCCAGCCG-TAATCGCA (SEQ ID: 4) (Ito, K et al. J. Biol. Chem. 1995, 270:958–965). Digoxigenin-labeled antisense RNA probes were synthesized using a RNA labeling kit (Boehringer, Mannheim, Germany) according to the manufacturers' instruction and the in situ hybridization protocol used with modifications as previously described. Arterial sections were deparafinized in xylene and rehydrated through graded ethanol solutions, washed, and treated with 5 $\mu$g/ml proteinase K (Boehringer) for 30 min at 37° C. The specimens were acetylated in 0.25% acetic anhydride in 0.1 M triethanolamine for 10 min at room temperature, partially dehydrated through graded ethanol solutions and briefly dried. Digoxigenin labeled RNA probes 1 mg/ml) were added in hybridization buffer (50% deionized formamide, 10 mM Tris-HCl (pH7.6), 0.6 M NaCl, 10% dextran sulphate, 1× Denhardt's solution, 0.25% SDS, 10 mM EDTA, 0.2 mg/ml Yeast total RNA) and slides were incubated at 60° C. under coverslips overnight. The coverslips were carefully removed and the sections were rinsed with 50% formamide solution. The hybridized probes were detected using an alkaline phosphatase conjugated anti-digoxigenin monoclonal antibody (Boehringer), and the colored product was visualized using Nitro Blue tetrazolium (Boehringer) and 5-bromo-4-chlor-indonyl-phosphate (Boehringer) as substrates. For color development, the sections were incubated for 30 minutes with a procollagen I probe and for 1 hour with a versican probe at room temperature. Slides were mounted with glycerin jelly and were kept at 4° C. Five random high-power microscopic fields (400×) of the adventitia per specimen were digitized (Color CCD Camera Model 2222-1040, COHU, San Diego, Calif.), and an image pixel analysis of the five data points per specimen was performed in a blinded fashion, by using a modification of a method described earlier (IP-lab spectrum, Scanalystics, Fairfax, Va.), to quantify and statistically evaluate differences in adventitial gene expression. In brief, a segmentation of stained (positive for gene expression) vs. unstained (negative for gene expression) areas per microscopic field was performed by setting a specific threshold value for all slides. The area of positive pixels is presented as a percentage of the area of all pixels per high power field. For statistical analysis, the median data point of every specimen was assessed and used to compare control versus PDT procollagen type I and veriscan gene expression.

Statistical Evaluation: All values are expressed as a mean ± SD. Differences between pairs of means were analyzed by means of a one-way analysis of variance (ANOVA) with Tukey's honestly significant test. Differences in adventitial cell numbers and mRNA expression were determined by means of the 2-tailed unpaired Student t test. Five data points per specimen were obtained for analyzing the mRNA expression. The media values for each specimen (N=3/group) were compared (Statistika, Statsoft, Tulsa, Okla.). Differences were considered significant at P<0.05 level.

Results

At harvest, all animals appeared healthy and without evidence of weight loss or wound infection. Animals treated with MB showed no signs of toxicity. No artery thrombosis was observed.

Figure 6A:
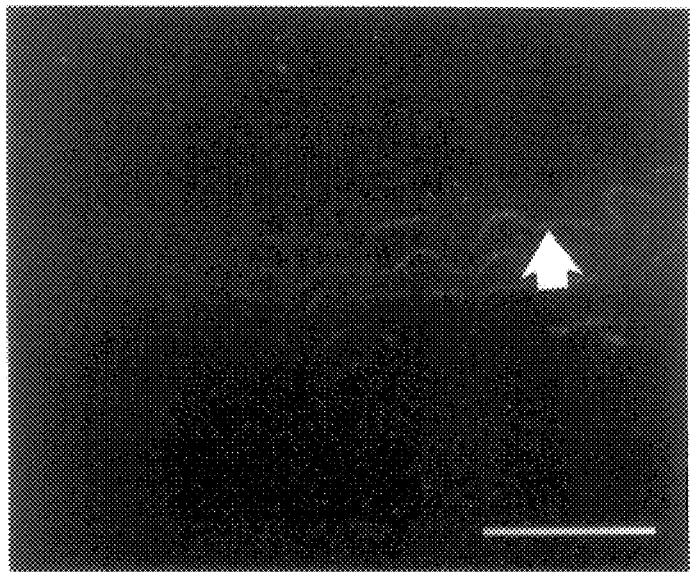
FIG. 6 depicts fluorescent micrographs of rat common carotid arteries directly after balloon-injury untreated (a) or after local delivery of 250 µg/ml methylene blue (b). Internal elastic lamina is noted. Excitation of unstained frozen sections was performed at 476 nm with a fluorescence capture between 620–630 nm. Note the high-fluorescence signal throughout the vessel wall after local delivery of the photosensitizer with the highest intensity in the medial layers close to the lumen. Scalebar equals 50 µm.
Figure 6B:
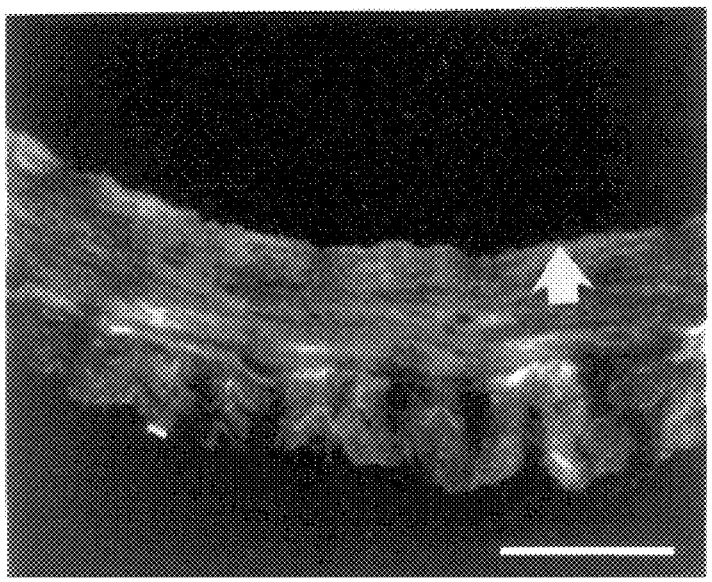

Fluorescence laser scanning confocal microscopy: FIG. 6 summarizes the findings of the distribution of MB in the carotid artery after local delivery. There was a faint background signal of the extracellular matrix in control arteries. However, 5 minutes after local delivery of dye, a strong homogenous fluorescent signal was detected in the entire thickness of the arterial wall. The highest intensity was seen in the medial layers closest to the lumen.

Figure 7A:
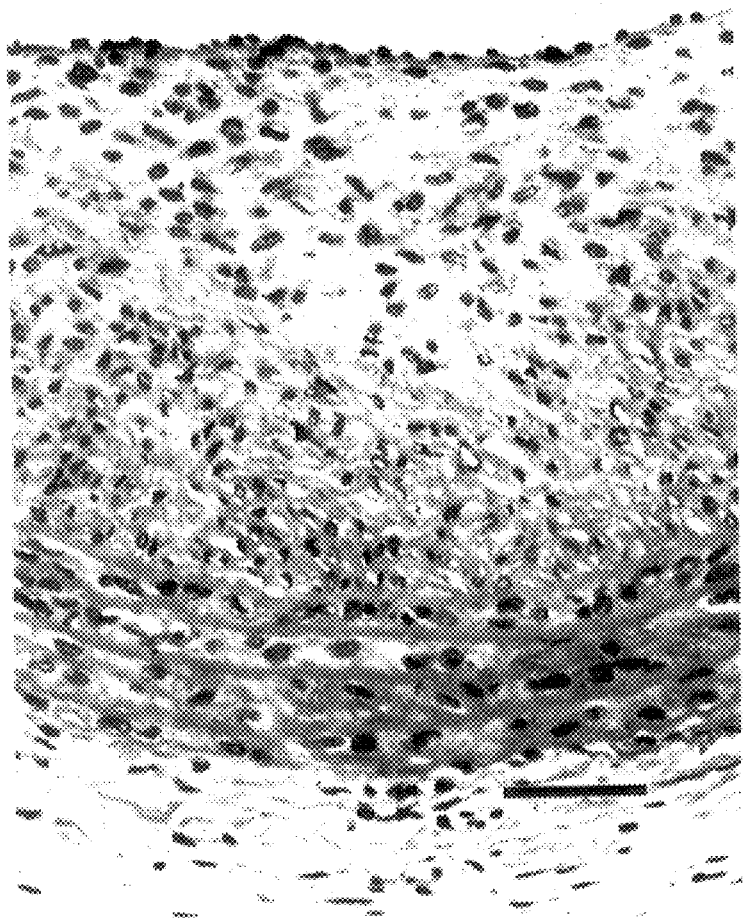
FIG. 7 depicts light micrographs of rat common carotid arteries stained with hematoxylin and eosin 2 weeks after balloon-injury untreated (a) or PDT-treated (b). Internal elastic lamina (arrow is noted. In PDT-treated arteries, no IH was seen, the media was cell free. Scalebar equals 50 µm.
Figure 7B:
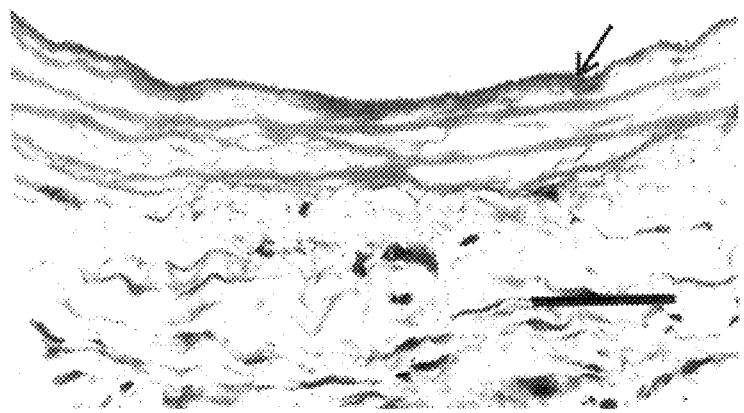

Light Microscopy and Vessel Histomorphometry: PDT-treated arteries presented with a denuded luminal surface with occasional platelets but without evidence of microthrombi, inflammation, or intimal thickening. The media was devoid of cells and consisted of a normal matrix tissue and a normal appearing elastic lamina. In contrast, IH formation was demonstrated in BI and PS. In these 2 groups, the media showed typical histomorphological architecture with several laminae, interspersed with cells. The adventitia of all groups was comprised of loose connective tissue interspersed with fibroblast like cells (FIGS. 7a–b). No significant difference in the number of adventitial cells per high power filed was noted (PDT: 39±9.4, BI: 45±6.3) and these cells occupied topographically similar positions.

The areas of IH in the BI and PS groups were revealed by morphometric analyses to be not significantly different (BI: 0.192±0.06 mm$^2$, PS: 0.183±0.05 mm$^2$) in contrast with the PDT groups that had no neointimal formation (0±0 mm$^3$, $P<0.0001$, Table 1). The media was markedly thickened after BI and PS (BI: 0.082±0.003 mm$^2$, PS: 0.085±0.005 mm$^2$), compared to PDT and uninjured control arteries (PDT: 0.063±0.004 mm$^2$, Control: 0.056±0.003 mm$^2$, $P<0.05$, Table 1). In all groups, no changes in vessel diameter were found at 2 weeks.

In Situ Hybridization

Figure 8A:
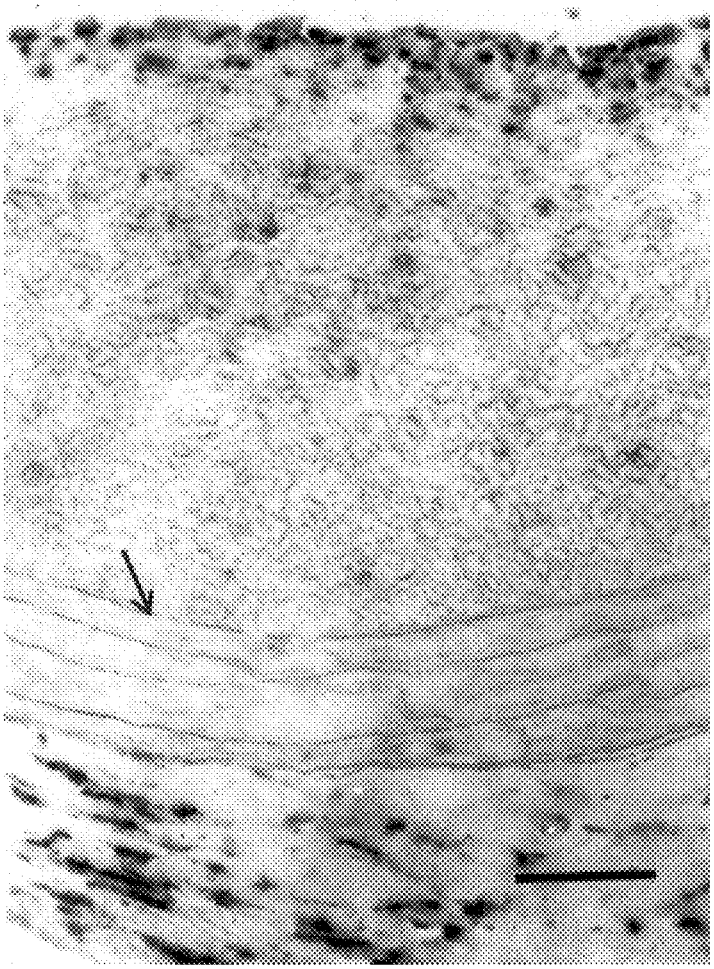
FIG. 8 depicts localization and quantitation of versican mRNA in the rat common carotid arteries stained 2 weeks after balloon-injury untreated (a) or PDT treated (b). Internal elastic lamina (arrow) is noted. Scalebar equals 50 µm.
Figure 8B:
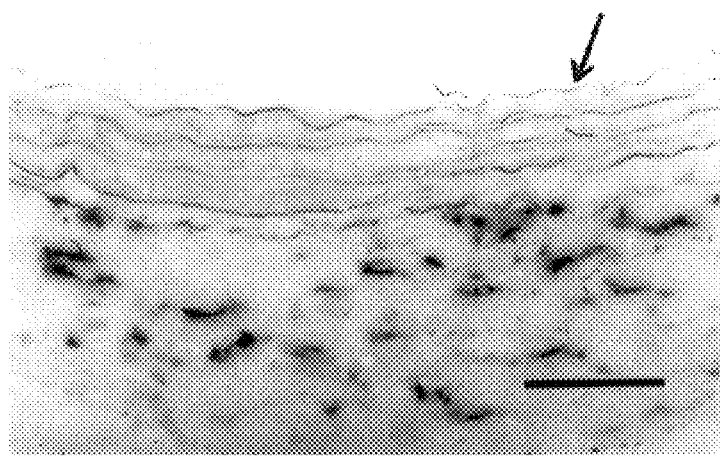

Versican: Uninjured control arteries did not express the proteoglycan versican in any layer of the arterial wall. Two weeks after balloon injury alone (BI), adventitial cells and cells in the innermost layers of the neointima expressed significant amounts of versican mRNA. The repopulating adventitial cells after PDT also expressed versican, but the quantity was significantly less (BI: 2.93%±0.61%, PDT: 1.13%±0.39%, $P<0.02$, FIGS. 8a and 8b).

Figure 9A:
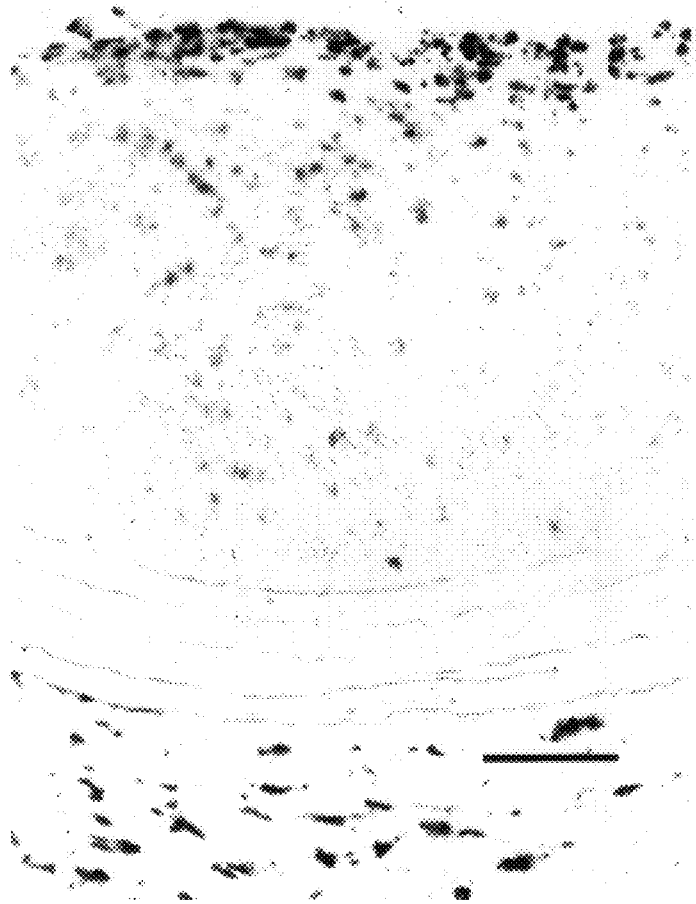
FIG. 9 shows localization and quantitation of procollagen type I mRNA in the rat carotid arteries stained 2 weeks after balloon-injury untreated (a) or PDT-treated (b). Internal elastic lamina (arrow) is noted. Scalebar equals 50 µm.
Figure 9B:
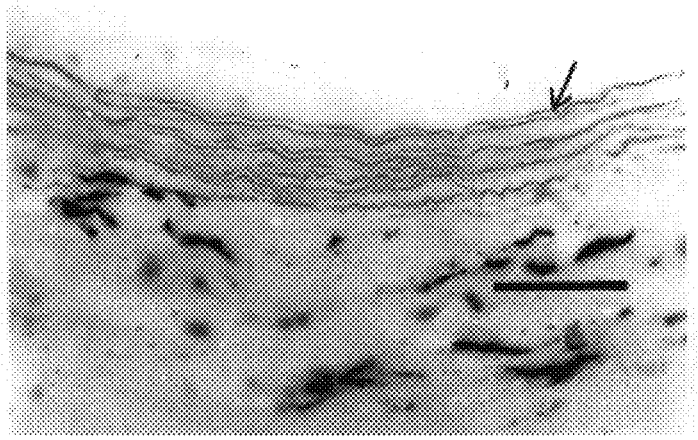

Pro-collagen type I: Uninjured control arteries did not express pro-collagen type I in any layer of the arterial wall. Two weeks after balloon injury alone (BI), adventitial cells and cells in the innermost layers of the neointima expressed significant amounts pro-collagen type I mRNA. The repopulation cells in the adventitia of PDT treated arteries expressed less pro-collagen type I mRNA, however this difference did not reach statistical significance (BI: 4.67%±1.02%, PDT: 4.13%±1.25%, $P<0.09$, FIGS. 9a and 9b).

Discussion

The occurrence of restenosis after all forms of reconstruction, whether interventional or surgical, remains an unsolved problem. The present method demonstrates that local delivery of the clinically available photosensitizer dye MB can be effectively used for vascular PDT to inhibit IH and favorably modulate the post-interventional vascular would healing response in vivo.

The development of IH following balloon injury of the rat carotid artery has been well studied. The simplicity of the rat model has facilitated analyses of the cellular response to injury and the identification of molecules that play a role in the pathogenesis of restenosis. Numerous vascular PDT studies have also utilized this model, and significant experience was acquired with regard to PDT dosimetry, histology, and healing responses. The ability of vascular PDT to inhibit IH in the rodent model was also confirmed in large animal models. However, these were short term experiments and the development of IH was not completely inhibited.

The development of post-interventional restenosis is a complex phenomenon and numerous initiating and perpetuating factors have been implicated. Recently, specific matrix molecules, such as procollagen type I and versican, have been implicated in modulating cell function and, therefore, modulating the development of restenosis. The upregulation of procollagen type I mRNA and subsequent production of collagen type I is a distinct phenomenon after arterial injury and has been associated with fibrosis and constrictive remodeling. Versican, a major chondroitin sulfate proteoglycan, is required for proliferation and migration of mesenchymal cells. Therefore, it plays a key role in the vascular injury healing response and also in atherogenesis. Versican mRNA production is also upregulated in nonhuman primate atherosclerotic arteries at 2 weeks after experimental angioplasty and has been shown to promote the development of restenosis in humans. The gene expression of both molecules was investigated in the present invention to understand the molecular aspects of the PDT-induced moldulation of vascular injury healing. Versican and pro-collagen type I are regulated on a pretranslational level, because the amount of mRNA expression and the amount of synthesized protein were found to be proportional. However, it has been shown that the accumulation of mature collagen type I depends not only on procollagen type I m RNA expression, but also on its posttranslational processing and collagen degradation. In the present invention, PDT of balloon-injured arteries resulted in a down-regulation of versican, which is an important factor for the successful long-term inhibition of restenosis by PDT after vascular injury. The presence of functional growth factors in the vascular wall is of major importance for the accumulation of proteoglycans such as versican. By its production of free radicals, PDT inactivates growth factors located in the vessel wall, which thereby result in lower gene expression of versican by the adventitial cells.

In contrast to versican, the gene expression of pro-collagen type I in the adventitia was not significantly affected by PDT. Collagen type I mRNA levels have been shown to be down-regulated by growth factors such as basic Fibroblast Growth Factor. This growth factor has been shown to be functionally inactivated in matrix following PDT and explains, in part, why there was no significant difference between PDT and balloon-injured control arteries in the quantity of pro-collage type I gene expression. In addition, although there is no statistical difference in gene expression, posttranslational mechanisms can lead to the different amounts of the protein in the PDT and control groups.

The morphologic appearance of the vessel 2 weeks after PDT with local delivery of MB is identical to that of PDT with different photosensitizers and different application modalities. These PDT-treated vessels demonstrate a lack of IH and an acellular media. In experiments with the clinically unavailable photosensitizer chloraluminum sulfonated phthalocyanin, inhibition of IH without arterial degeneration was shown for as long as 6 months after PDT, and is considered that MB is as effective.

For vascular PDT, photosensitizers have been successfully administered systemically in different animal models. Despite the selectivity of confined light irradiation, the site-specific delivery of a photosensitizer directly into a site of vascular intervention has conceptual appeal. First, it would achieve specific local drug concentrations. Second, concentrating the drug at the target site and thus avoiding substantial systemic dosing could minimize systemic adverse effects. Third, by utilizing specific local, luminal delivery parameters, the photosensitizer can be confined to predetermined layers of the artery wall.

An important aspect of site-specific drug delivery and PDT is the concern of combined balloon-injury, pressure-delivery and PDT, all discrete injuries to the vascular wall. Data provides that infusion with pressures of 180 mm Hg were both atraumatic and sufficient for the uptake of the dye. Previous work has shown that even short-term pressurization up to 400 mm Hg in the rat carotid artery for photosensitizer delivery did not induce injury to the arterial wall structure. The vessel wall thickness in this model is much smaller than that of a human vessel and did not support the use of specialized delivery catheters, developed for human size vessels. However, double-balloon catheters, which create a protected space at the site of delivery that allows for prolonged balloon inflation and prolonged drug delivery, have been successfully shown to deliver drugs to arteries in a pig model without creating measurable injury. As with the double balloon-catheter, a sealed compartment was created in the rat carotid artery using vessel clamps to introduce MB at an elevated pressure. Novel microporous catheter systems, which offer improved functional characteristics compared to porous balloons, are being developed in an effort to improve effective local delivery of drugs to human size vessels and to minimize additional injury to the arterial wall.

As in many experimental studies, limitations of the present method may be related to the animal model and the delivery mode used. The rat carotid artery balloon injury model produces considerable IH and mRNA expression of fibroproliferative factors, which have been shown to play an important role in the human vascular injury response. However, the response in this model may not represent the prototype of a restenotic lesion in humans. Due to different artery size and the presence of arteriosclerotic plaque, the local application of drugs to human arteries may require modified devices which are adapted by those skilled in the art. Nevertheless, vascular PDT utilizing a local drug delivery concept with a clinically available photosensitizer inhibits the development of IH an deceased adventitial cell versican gene expression. It can be performed safely is a viable strategy to prevent restenosis in humans.

One skilled in the art will appreciate further features and advantages of the invention based on the above-described embodiments. Accordingly, the invention is not to be limited by what has been particularly shown and described, except as indicated by the appended claims. Such equivalents are intended to be encompassed in the scope of the following claims. All publications and references cited herein including those in the background are expressly incorporated herein by reference in their entirety.

What is claimed is:

1. A method for modulating restenosis in a subject, comprising the steps of non-systemically administering a therapeutically effective amount of a benzoporphyrin derivative or methylene blue to an injury site in vivo and irradiating the injury site with sufficient light energy between about 300 and 900 nm, such that undesired cells at the injury site are destroyed and restenosis in the subject is modulated.

2. The method of claim 1, wherein the light energy is delivered by a high energy light source.

3. The method of claim 2, wherein the high energy light source is a laser.

4. The method of claim 1, wherein the therapeutically effective amount of the benzoporphyrin derivative is between about 0.5 µg/ml and about 25 µg/ml.

5. The method of claim 4, wherein the light energy is about 100 J/cm$^2$.

6. The method of claim 1, wherein the therapeutically effective amount of the methylene blue is between about 5 µg/ml and about 1000 µg/ml.

7. The method of claim 6, wherein the light energy is about 100 J/cm$^2$.

8. A method for modulating intimal hyperplasia in a subject, comprising the steps of non-systemically administering a therapeutically effective amount of a benzoporphyrin derivative or methylene blue to undesired cells of a target tissue site in vivo and irradiating the undesired cells of the target tissue treated injury site with a sufficient amount of light energy between about 300 and 900 nm, such that the undesired cells of the target tissue are eradicated.

9. The method of claim 8, wherein the light energy is delivered by a high energy light source.

10. The method of claim 9, wherein the high energy light source is a laser.

11. The method of claim 8, wherein the therapeutically effective amount of the benzoporphyrin derivative is between about 0.5 µg/ml and about 25 µg/ml.

12. The method of claim 11, wherein the light energy is about 100 J/cm$^2$.

13. The method of claim 8, wherein the therapeutically effective amount of the methylene blue is between about 5 µg/ml and about 1000 µg/ml.

14. The method of claim 13, wherein the light energy is about 100 J/cm$^2$.

15. The method of claim 8, wherein the target tissue site is the subluminal space of a blood vessel and the cells are selected from the group consisting of smooth muscle cells, fibroblasts, myoblasts, and combinations thereof.

* * * * *

SEQUENCE LISTING

<160> NUMBER OF SEQ ID NOS: 4

<210> SEQ ID NO 1
<211> LENGTH: 24
<212> TYPE: DNA
<213> ORGANISM: murine

<400> SEQUENCE: 1
tgacttcagc ttcctgcctc agcc                                    24

<210> SEQ ID NO 2
<211> LENGTH: 47
<212> TYPE: DNA
<213> ORGANISM: murine

<400> SEQUENCE: 2
taatacgact cactataggg aggccctgga ggagcagggc cttcttg            47

<210> SEQ ID NO 3
<211> LENGTH: 25
<212> TYPE: DNA
<213> ORGANISM: murine

<400> SEQUENCE: 3
ggagacgact gtcttggtgg cccag                                   25

<210> SEQ ID NO 4
<211> LENGTH: 42
<212> TYPE: DNA
<213> ORGANISM: murine

<400> SEQUENCE: 4
taatacgact cactataggg aggacagcca gccgtaatcg ca                42